US009872824B2

(12) United States Patent
Kadir et al.

(10) Patent No.: US 9,872,824 B2
(45) Date of Patent: Jan. 23, 2018

(54) SEMI-PERMANENT HAIR STRAIGHTENING COMPOSITION AND METHOD

(71) Applicant: Lubrizol Advanced Materials, Inc., Cleveland, OH (US)

(72) Inventors: Murat Kadir, Brecksville, OH (US); Mark J. McGuiness, Chagrin Falls, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 0 days.

(21) Appl. No.: 14/766,217

(22) PCT Filed: Feb. 3, 2014

(86) PCT No.: PCT/US2014/014409
§ 371 (c)(1),
(2) Date: Aug. 6, 2015

(87) PCT Pub. No.: WO2014/123805
PCT Pub. Date: Aug. 14, 2014

(65) Prior Publication Data
US 2015/0374604 A1    Dec. 31, 2015

Related U.S. Application Data

(60) Provisional application No. 61/761,326, filed on Feb. 6, 2013.

(51) Int. Cl.
*A61K 8/49* (2006.01)
*A61Q 5/06* (2006.01)
*A61Q 5/12* (2006.01)
*A61Q 5/04* (2006.01)

(52) U.S. Cl.
CPC .............. *A61K 8/4973* (2013.01); *A61K 8/49* (2013.01); *A61Q 5/06* (2013.01); *A61Q 5/04* (2013.01); *A61Q 5/12* (2013.01)

(58) Field of Classification Search
CPC .................................. A61K 8/49; A61K 8/4973
See application file for complete search history.

(56) References Cited

U.S. PATENT DOCUMENTS

| 3,966,903 A | 6/1976 | Torii et al. |
| 6,384,280 B1* | 5/2002 | Cherpeck .............. C07C 213/00 564/353 |
| 2008/0075681 A1 | 3/2008 | Cassier et al. |
| 2008/0118455 A1* | 5/2008 | Takahashi ............ A61K 8/4973 424/70.5 |
| 2011/0146699 A1* | 6/2011 | Saute ........................ A45D 7/06 132/206 |
| 2014/0014130 A1* | 1/2014 | Savaides .................. A61K 8/21 132/206 |
| 2016/0367462 A1* | 12/2016 | Samain ................ A61K 8/4946 |

FOREIGN PATENT DOCUMENTS

| DE | 102005017913 A1 | 10/2006 |
| FR | 2847473 A1 | 5/2004 |
| FR | 2978038 | * 1/2013 |
| JP | 2007-176796 A1 | 7/2007 |
| WO | WO2006/111255 | * 10/2006 |
| WO | 2013/125053 A1 | 8/2013 |
| WO | WO 2013/144263 | * 10/2013 |

OTHER PUBLICATIONS

Machine Translation of claims and description for FR 2978038-PD Jan. 25, 2013.*
Chen (Materials 2014, 7, 6158-6168).*
Durgam (Health Hazard Evaluation Report HETA 2011-0014-3147, Nov. 2011, p. 2).*
Brazilian Blowout Treatment Summary (Nov. 2013).*

* cited by examiner

*Primary Examiner* — Valerie Rodriguez-Garcia
(74) *Attorney, Agent, or Firm* — Thoburn T. Dunlap

(57) ABSTRACT

A composition and a process for straightening hair are disclosed. The process includes coating keratin fibers with a composition comprising a thermally-activated agent and contacting the coated keratin fibers with a heating device at a temperature of at least 185° C. for sufficient time to modify the keratin fibers. The thermally-activated agent comprises a heterocyclic compound containing two heteroatoms selected from nitrogen and oxygen in a 5 or 6-membered ring, such as a cyclic alkylene carbonate.

11 Claims, No Drawings

SEMI-PERMANENT HAIR STRAIGHTENING COMPOSITION AND METHOD

CROSS REFERENCE TO RELATED APPLICATION

This application claims priority from PCT Application Serial No. PCT/US2014/014409 filed on Feb. 3, 2014, which claims the benefit of U.S. Provisional Application No. 61/761,326 filed on Feb. 6, 2013.

BACKGROUND

The exemplary embodiment relates to a method for straightening hair by application of heat and to a composition which can be activated by heat comprising a heterocyclic compound containing two heteroatoms selected from nitrogen and oxygen in a 5 or 6-membered ring, such as a cyclic alkylene carbonate.

Various methods are available for semi-permanent and permanent straightening of hair which can maintain the hair in a modified state for several washes. Many of the permanent treatment methods make use of harsh chemicals which can be hazardous to those performing and receiving the treatment or which give off unpleasant odors. Some of these methods are based on cleavage of the cysteine disulfide covalent bonds that are present in keratin. In one method, the disulfide bonds are first broken with a reducing agent. Then a fixative, such as hydrogen peroxide, is applied while the hair is under tension to reconstitute the disulfide bonds in a different arrangement. The peroxide can cause damage to the hair and scalp. Other methods use a hydroxide base which replaces the disulfide bonds ($-CH_2-S-S-CH_2-$) with lanthionine bonds ($-CH_2-S-CH_2-$) in a two stage process using a hydroxide ion in the first step and a thiol group in the second. The hydroxide is used at fairly high concentrations and can cause scalp burning, and irritation or damage of the eyes and nose. Thiols leave the hair with an unpleasant odor and can lead to degradation of the hair fibers.

Semi-permanent methods use a cross-linking agent to form bonds while the hair is heated. Formaldehyde, for example, is used in many commercial straightening products, either as an ingredient of the composition or as a reaction product that is formed on heating of the hair. However, it can cause allergic reactions to the skin, eyes and lungs, can cause severe damage to the eyes, and poses other health risks. The use of formaldehyde in hair straightening compositions has been discouraged or banned in some countries but it remains in widespread use, due to its effectiveness. Relaxing compositions including a denaturing agent such as urea have also been proposed. However, while urea is less caustic than a hydroxide-based composition, it can decompose to ammonia and poisonous isocyanic acid at the high temperatures used for thermal hair straightening.

BRIEF DESCRIPTION

In accordance with one aspect of the exemplary embodiment, a process for straightening hair includes coating keratin fibers with a composition comprising a thermally-activated agent and contacting the coated keratin fibers with a heating device at a temperature of at least 185° C. for sufficient time to modify the keratin fibers. The thermally-activated agent has the general formula of Structure (I):

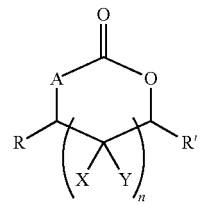

Structure (I)

where:
A is selected from N and O;
R and R' are independently selected from H, $CH_3$, $CH_2CH_3$, and $CH_2OH$;
X and Y are independently selected from H and alkyl; and
n=0 or 1.

In another aspect, a composition for straightening hair includes a solvent and at least 15 wt. % of a thermally-activated agent, the thermally-activated agent having the general formula of Structure (I):

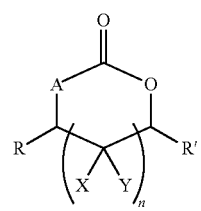

Structure (I)

where:
A is selected from N and O;
R and R' are independently selected from H, $CH_3$, $CH_2CH_3$, and $CH_2OH$;
X and Y are independently selected from H and alkyl; and
n=0 or 1; and
at least one of a cationic surfactant and a rheology modifier,
the composition having a pH of less than 7.5 and a viscosity of at least 400 cps.

DETAILED DESCRIPTION

Aspects of the exemplary embodiment relate to a semi-permanent hair straightening composition and method of use. The exemplary composition includes at least one thermally-activated agent which can be present, in total, at up to 95 wt. % or up to 70 wt. % of the composition and may further include a solvent/diluent in which the thermally-activated agent is soluble or dispersible. By "thermally-activated" it is meant that the agent can be activated by heat, as in a hair-straightening process, although the term is not intended to be considered as limiting the mode of operation of the agent in the composition. The composition may be in the form of a liquid, cream, mousse, gel, spray, or the like.

In another aspect, a process for straightening keratin fibers, such as human hair, includes contacting the keratin fibers with the exemplary composition to coat the fibers, maintaining the keratin-fibers in contact with the composition for sufficient time to effect straightening when the fibers are heated, and optionally drying the fibers to remove at least some of the solvent. The keratin fibers, coated with the composition, are contacted with a surface of a heating device, such as a flat iron, having a temperature of from 185-230° C. for sufficient time to relax the keratin fibers, e.g., by reaching the glass transition temperature, which can vary, to some degree, depending on the moisture content. The relaxation generally results in an increase in the average length of the keratin fibers, as measured when a lock of the curly fibers is suspended from a support, of at least 5% or at least 10%, which can be maintained over several hair washing treatments (involving shampooing and drying the hair), such as at least 10 or at least 20 washes. The exemplary process is semi-permanent in that over time, the straightened fibers begin to return to their original, curly state. While the method can be used to form very straight hair, it can also be used in a process in which a semi-permanent wave is created.

The thermally-activated agent used in the semi-permanent hair straightening composition and process is a heterocyclic compound having the general formula shown as Structure (I):

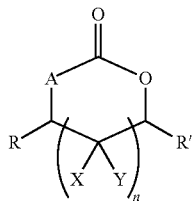

Structure (I)

where

A is selected from N (nitrogen) and O (oxygen);

R and R' are independently selected from H, $CH_3$, $CH_2CH_3$ and $CH_2OH$;

X and Y are independently selected from H and alkyl, such as a $C_1$-$C_6$ or $C_1$-$C_3$ alkyl group, such as $CH_3$; and n=0 or 1.

In one embodiment, A=O. The structure thus represents an alkylene carbonate.

In one embodiment, at least one of R and R'=H. In another embodiment, both R and R'=H.

In one embodiment, n=0, i.e., the structure represents a five-membered ring of the general formula shown as Structure (II):

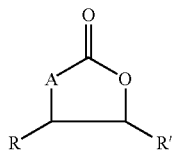

Structure (II)

where A, R and R' are as defined above.

As one example, the alkylene carbonate can be of the general form of Structure (III):

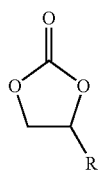

Structure (III)

where R is as above.

Five-membered alkylene carbonates (1,3-dioxolan-2-ones), such as ethylene carbonate ("EC", where R and R'=H), propylene carbonate (R=$CH_3$ and R'=H), butylene carbonate (where R=$CH_2CH_3$ and R'=H or where R=$CH_3$ and R'=$CH_3$), and glycerol carbonate (R=$CH_2OH$ and R'=H) are exemplary thermally-activated agents useful herein.

In one embodiment, when n=1, at least one or both X and Y=H.

Six-membered alkylene carbonates (1,3-dioxan-2-ones) useful herein include trimethylene carbonate (X and Y=H, R and R'=H). Exemplary thermally-activated agents where A=N include 2-oxazolidinone (R and R'=H, n=0) and derivatives thereof.

Exemplary thermally-activated agent(s) according to structure (I) are small molecules (MW≤800 g/mol, or ≤600 g/mol, such as ≤200 g/mol) rather than oligomeric compounds or polymers (≥1000 g/mol). They are water compatible and stable, able to penetrate and react with keratinous materials, and can be activated by a flat or round iron at ≤210° C.

Compounds of Structure (I), such as alkylene carbonates, are particularly suited to the exemplary application as they generally have low toxicity and do not form toxic byproducts during the heating stage. They are also highly soluble in water at room temperature (25° C.), with ethylene carbonate being highly soluble (concentrations over 50 wt. % in water being readily feasible) and propylene carbonate being soluble in lesser amounts (up to about 20 wt. %).

In one embodiment, the thermally-activated agent(s) according to structure (I) is/are present in the straightening composition at a concentration of at least 5 wt. %, or at least 7 wt. %, or at least 10 wt. %, or at least 12 wt. %, or at least 15 wt. %, or at least 18 wt. %, and in some embodiments, the thermally-activated agent is present in the straightening composition at a concentration of up to 95 wt. %, or up to 70 wt. %, or up to 55 wt. %, or up to 50 wt. %, or up to 40 wt. %, or up to 35 wt. %, or up to 30 wt. %. In example formulations disclosed herein, the thermally-activated agent is selected from ethylene carbonate (1,3-dioxolan-2-one), propylene carbonate, glycerol carbonate, trimethylene carbonate, 2-oxazolidinone and combinations thereof. In such cases, the thermally-activated agent may suitably be present in the composition at a total concentration of 10-40 wt. %, or at least 15 wt. %.

In one embodiment, the thermally-activated agent includes a mixture of ethylene carbonate and propylene carbonate at a weight ratio of from 95/5 to 5/95, such as at least 10/90. In such embodiments, the propylene carbonate may replace some or all of other solvents used in the composition.

Alkylene carbonates suitable for use herein are available from Huntsman Corporation under the tradename JEFFSOL® alkylene carbonates. JEFFSOL ethylene carbonate is solid at room temperature. JEFFSOL EC-75, EC-50, and EC-25 are blends of JEFFSOL ethylene carbonate and propylene carbonate in the ratios of 75/25, 50/50 and 25/75 by weight, respectively. These blends are liquid at room temperature. As sold, these products are said to be at least 99.8% pure. Higher purity versions are also available.

U.S. Pat. No. 2,873,282 describes methods for making alkylene carbonates by reacting an alkylene oxide or compound thereof with carbon dioxide. U.S. Pat. No. 2,773,070 describes similar methods. Typically, an alkylammonium halide catalyst such as tetraethylammonium bromide is employed. Glycerol (glycerin) carbonate (GC) is available commercially and can be synthesized by the reaction of glycerin with a carbonate source such as phosgene, a dialkyl carbonate, or an alkylene carbonate; by reaction of glycerin with urea, carbon dioxide, and oxygen; or by reaction of carbon dioxide with glycidol.

In one embodiment, the composition (and treatment process described herein) is free or substantially free (less than 1 wt. %, such as less than 0.1 wt. %) of thermally-activated agents/cross-linking agents other than those of Structure (I). In the exemplary embodiment, the thermally-activated agent(s) of Structure (I) is the sole thermally-activated agent. In particular, the composition and method are free or substantially free formaldehyde. The exemplary method and composition use no formaldehyde either directly, in the composition, or through reaction, during the method, of any sources of formaldehyde. Similarly, the composition and process may be free or substantially free of glyoxylic acid, urea, and derivatives thereof, which can break down to form irritants.

In one embodiment, the composition (and treatment process described herein) is free or substantially free (less than 1 wt. %, or less than 0.1 wt. %, or less than 0.01 wt. %) of cyclic mercapto (thiol) group-containing compounds. Cyclic mercapto group-containing compounds are cyclic compounds containing an S—H group linked directly to a ring carbon atom. In one embodiment the composition (and treatment method described herein) is free or substantially free (less than 1 wt. %, such as less than 0.1 wt. %) of all compounds which contain thiol groups, including aliphatic and cyclic thiol group-containing compounds.

In one embodiment, the composition and process are free or substantially free (less than 1 wt. %, or less than 0.1 wt. %, or less than 0.01 wt. %) of sulfites which can break the bisulfide bond in the keratin fibers (that are typically used in permanent waving compositions).

Solvent/Diluent

In addition to the one or more thermally-activated agents present, the composition may include a solvent in which the thermally-activated agent(s) is soluble/dispersible. The solvent may be selected from water, and combinations thereof. Specific examples include water and/or ethanol.

The composition can be prepared as water-free or water-based formulations, and formulations containing water-miscible auxiliary solvents and/or diluents are also contemplated.

Useful solvents commonly employed are typically liquids, such as water (deionized, distilled or purified), alcohols, such as $C_1$-$C_{10}$ aliphatic and aromatic alcohols (including diols and triols, such as glycols, e.g., ethylene glycol, propylene glycol, and glycerin), polyols, and the like, and mixtures thereof.

Examples of solvents, other than water, include linear and branched alcohols, such as ethanol, propanol, isopropanol, hexanol, and the like; and aromatic alcohols, such as benzyl alcohol, cyclohexanol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Other examples of non-aqueous solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents or diluents may also serve as conditioners and emulsifiers. For purposes of computing a weight basis in the composition, however, all of the liquids listed in this section are considered as solvents/diluents.

pH Modifiers

The pH of the composition can be from to 1.5-9.5, e.g., at least 4.5, or at least 5.5. In some embodiments, the pH is up to 8.5, or up to 7.5, or up to 6.5. To provide the selected pH, the composition may include one or more pH modifiers selected from organic and inorganic acids and bases.

The pH of the composition can be adjusted with any combination of acidic and/or basic pH adjusting agents known to the art. Acidic materials include organic acids and inorganic acids, in particular, monocarboxylic acids, dicarboxylic acids, and tricarboxylic acids, for example, acetic acid, citric acid, tartaric acid, alpha-hydroxy acids, beta-hydroxy acids, salicylic acid, lactic acid, malic acid, glycolic acid, amino acids, and natural fruit acids, or inorganic acids, for example, hydrochloric acid, nitric acid, sulfuric acid, sulfamic acid, phosphoric acid, and combinations thereof.

Basic materials include inorganic and organic bases, and combinations thereof. Examples of inorganic bases include but are not limited to the alkali metal hydroxides (especially sodium, potassium, and ammonium), and alkali metal salts such as sodium borate (borax), sodium phosphate, sodium pyrophosphate, and the like; and mixtures thereof. Examples of organic bases include triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, trometamine (2-amino 2-hydroxymethyl-1,3-propanediol), and PEG-15 cocamine.

Such pH modifiers may be present at from 0.0001 wt. % to 50 wt. %, based on the active component.

Auxiliary Components of the Composition

The composition may include one or more auxiliary components, such as rheology modifiers, surfactants, emulsifiers, conditioning agents, humectants, emollients, preservatives, chelating agents, propellants, fragrance, botanicals, hair fixing agents, colorants, combinations thereof, and the like.

1. Rheology Modifiers

To provide a composition which adheres well to the hair fibers, the composition can include a rheology modifier which increases the overall viscosity of the composition. The viscosity of the composition, when applied to the hair, can be at least 400 cPs, or at least 1000 cPs, or at least 2000 cPs, or at least 3000 cPs, and can be up to 10,000 cPs.

To increase the viscosity, the composition may include one or more rheology modifiers, which can be synthetic or natural.

Examples include fatty alcohols, such as $C_{10}$-$C_{32}$ alcohols, e.g., $C_{12}$-$C_{22}$ alcohols, natural oils, and polymers of acrylic acid and/or methacrylic acid, such as carbomers. Exemplary natural oils include mineral oils (mainly $C_{15}$-$C_{40}$ linear and branched aliphatic alkanes, with minor amounts of cycloalkanes), which may be sold as paraffinum liquidum.

Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule, wherein in one aspect the substituent is independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. No. 5,087,445; U.S. Pat. No. 4,509,949; and U.S. Pat. No. 2,798,053.

In one aspect, the AST rheology modifier or thickener is a crosslinked homopolymer polymerized from acrylic acid or methacrylic acid and is generally referred to under the INCI name of Carbomer. Commercially available Carbomers include Carbopol® polymers 934, 940, 941, 956, 980, and 996 available from Lubrizol Advanced Materials, Inc. In a further aspect, the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect, the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc.

In another aspect, the auxiliary rheology modifier can be a crosslinked, linear poly(vinyl amide/acrylic acid) copolymer as disclosed in U.S. Pat. No. 7,205,271, the disclosure of which is herein incorporated by reference.

Another class of synthetic rheology modifiers suitable for use in the composition includes hydrophobically modified ASTs, commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect, associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, iso-octyl alcohol (2-ethyl hexanol), pelargonic alcohol (1-nonanol), decyl alcohol, lauryl alcohol, myristyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843. In addition, an extensive review of HASE polymers is found in Gregory D. Shay, Chapter 25, "Alkali-Swellable and Alkali-Soluble Thickener Technology A Review", Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. Commercially available HASE polymers are sold under the trade names, Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer) from Rohm & Haas, and Novethix™ L-10 (INCI Name: Acrylates/Beheneth-25 Methacrylate Copolymer) from Lubrizol Advanced Materials, Inc.

In another embodiment, acid swellable associative polymers can be used with the hydrophobically modified, cationic polymers of the present invention. Such polymers generally have cationic and associative characteristics. These polymers are free radical addition polymers polymerized from a monomer mixture comprising an acid sensitive amino substituted hydrophilic monomer (e.g., dialkylamino alkyl(meth)acrylates or (meth)acrylamides), an associative monomer (defined hereinabove), a lower alkyl(meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from 0.5 to 6.5. Exemplary acid swellable associative polymers are commercially available under the trade name Structure® Plus (INCI Name: Acrylates/Aminoacrylates/$C_{10}$-$C_{30}$ Alkyl PEG-20 Itaconate) from Akzo Nobel, and Carbopol® Aqua CC (INCI Name: Polyacrylates-1 Crosspolymer) from Lubrizol Advanced Materials, Inc. In one aspect, the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/PPG-30/5 allyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479.

Hydrophobically modified alkoxylated methyl glucosides, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Glucamate™ SSE-20, respectively, are also suitable as rheology modifiers.

Polysaccharides obtained from tree and shrub exudates, such as gum Arabic, gum gahatti, and gum tragacanth, as well as pectin; seaweed extracts, such as alginates and carrageenans (e.g., lambda, kappa, iota, and salts thereof); algae extracts, such as agar; microbial polysaccharides, such as xanthan, gellan, and wellan; cellulose ethers, such as ethylhexylethylcellulose, hydroxybutylmethylcellulose, hydroxyethylmethylcellulose, hydroxypropylmethylcellulose, methylcellulose, carboxymethylcellulose, hydroxyethylcellulose, and hydroxypropylcellulose; polygalactomannans, such as fenugreek gum, cassia gum, locust bean gum, tara gum, and guar gum; starches, such as corn starch, tapioca starch, rice starch, wheat starch, potato starch and sorghum starch can also be employed in the compositions herein as suitable rheology modifiers.

The rheology modifier(s) can be used alone or in combination and may be present in the composition, on an actives basis, at a total concentration of 0.001-50 wt. %, e.g., at least 0.1 wt. %, or at least 1 wt. %, such as up to 20 wt. %, or up to 10 wt. %%, or up to 3 wt. %, based on the total weight of the composition.

2. Surfactants

The composition may also include one or more surfactants, such as anionic, cationic, amphoteric, and nonionic surfactants, as well as mixtures thereof.

Cationic surfactants present may act as conditioning agents and assist in the heating step by ensuring that the heating device runs smoothly over the hair fibers. While the surfactants may also help to increase viscosity, they are not considered as rheology modifiers for purposes of describing the exemplary embodiment herein.

The cationic surfactants can be any of the cationic surfactants known or previously used in the art of aqueous surfactant compositions. Suitable classes of cationic surfactants alkyl amines, alkyl imidazolines, ethoxylated amines, quaternary compounds, and quaternized esters. In addition, alkyl amine oxides can function as a cationic surfactant at a low pH.

Alkylamine surfactants can be salts of primary, secondary and tertiary fatty $C_{12}$-$C_{22}$ alkylamines, substituted or unsubstituted, and substances sometimes referred to as "amidoamines". Examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Examples of amidoamines and salts thereof include stearamido propyl dimethyl amine, stearamidopropyl dimethylamine citrate, palmitamidopropyl diethylamine, and cocamidopropyl dimethylamine lactate.

Examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Examples of ethyoxylated amines include PEG-cocopolyamine, PEG-15 tallow amine, quaternium-52, and the like.

Among the quaternary ammonium compounds useful as cationic surfactants, some correspond to the general formula: $(R^5R^6R^7R^8N^+)$ $E^-$, wherein $R^5$, $R^6$, $R^7$, and $R^8$ are independently selected from an aliphatic group having from 1 to about 22 carbon atoms, or an aromatic, alkoxy, polyoxyalkylene, alkylamido, hydroxyalkyl, aryl or alkylaryl group having 1 to about 22 carbon atoms in the alkyl chain; and $E^-$ is a salt-forming anion such as those selected from halogen, (e.g., chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher ($C_{10}$-$C_{32}$ in the alkyl chain), can be saturated or unsaturated. In one aspect, the aryl groups are selected from phenyl and benzyl.

Exemplary quaternary ammonium surfactants include, but are not limited to cetyl trimethylammonium chloride (cetrimonium chloride), cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride (behentrimonium chloride), benzalkonium chloride, benzethonium chloride, and di(coconutalkyl) dimethyl ammonium chloride, ditallowdimethyl ammonium chloride, di(hydrogenated tallow)dimethyl ammonium chloride, di(hydrogenated tallow)dimethyl ammonium acetate, ditallowdimethyl ammonium methyl sulfate, ditallow dipropyl ammonium phosphate, and ditallow dimethyl ammonium nitrate.

At low pH, amine oxides can protonate and behave similarly to N-alkyl amines. Examples include, but are not limited to, dimethyl-dodecylamine oxide, oleyldi(2-hydroxyethyl)amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

Particularly useful cationic surfactants include fatty acid derivatives, such as fatty ($C_{10}$-$C_{32}$ in the alkyl chain) alkylammonium chlorides, such as cetrimonium chloride and behentrimonium chloride. Such surfactants may also serve as conditioning agents and emollients.

Other surfactants may be present as various components, such as substantially insoluble materials requiring suspension or stabilization (e.g., a silicone, an oily material, a pearlescent material, aesthetic and cosmeceutical beads and particles, gaseous bubbles, exfoliants, and the like), may be present in the composition.

The anionic surfactant can be any of the anionic surfactants known or previously used in the art of aqueous surfactant compositions. Suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulphates, alkyl monoglyceryl ether sulfates, alkyl monoglyceride sulfates, alkyl monoglyceride sulfonates, alkyl succinates, alkyl sulfosuccinates, alkyl sulfosuccinamates, alkyl ether sulphosuccinates, alkyl amidosulfosuccinates; alkyl sulphoacetates, alkyl phosphates, alkyl ether phosphates, alkyl ether carboxylates, alkyl amidoethercarboxylates, N-alkylamino acids, N-acyl amino acids, alkyl peptides, N-acyl taurates, alkyl isethionates, carboxylate salts wherein the acyl group is derived from fatty acids; and the alkali metal, alkaline earth metal, ammonium, amine, and triethanolamine salts thereof.

In one aspect, the cation moiety of the forgoing salts is selected from sodium, potassium, magnesium, ammonium, mono-, di- and triethanolamine salts, and mono-, di-, and tri-isopropylamine salts. The alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; sodium, potassium, lithium, magnesium, and triethanolamine lauryl sulfate, coco sulfate, tridecyl sulfate, myristyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium $C_{12}$-$C_{14}$ olefin sulfonate, sodium laureth-6 carboxylate, sodium methyl cocoyl taurate, sodium cocoyl glycinate, sodium myristyl sarcosinate, sodium dodecylbenzene sulfonate, sodium cocoyl sarcosinate, sodium cocoyl glutamate, potassium myristoyl glutamate, triethanolamine monolauryl phosphate, and fatty acid soaps, including the sodium, potassium, ammonium, and triethanolamine salts of a saturated and unsaturated fatty acids containing from about 8 to about 22 carbon atoms.

Amphoteric or zwitterionic surfactants are molecules that contain acidic and basic moieties and have the capacity of behaving either as an acid or a base. Suitable surfactants can be any of the amphoteric surfactants known or previously used in the art of aqueous surfactant compositions. Exemplary amphoteric surfactant classes include but are not limited to amino acids (e.g., N-alkyl amino acids and N-acyl amino acids), betaines, sultaines, and alkyl amphocarboxylates.

Amino acid based surfactants suitable herein include surfactants represented by the formula:

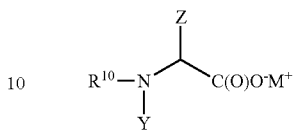

wherein $R^{10}$ represents a saturated or unsaturated hydrocarbon group having 10 to 22 carbon atoms or an acyl group containing a saturated or unsaturated hydrocarbon group having 9 to 22 carbon atoms, Y is hydrogen or methyl, Z is selected from hydrogen, —$CH_3$, —$CH(CH_3)_2$, —$CH_2CH(CH_3)_2$, —$CH(CH_3)CH_2CH_3$, —$CH_2C_6H_5$, —$CH_2C_6H_4OH$, —$CH_2OH$, —$CH(OH)CH_3$, —$(CH_2)_4NH_2$, —$(CH_2)_3NHC(NH)NH_2$, —$CH_2C(O)O^-M^+$, —$(CH_2)_2C(O)O^-M^+$. M is a salt forming cation. In one aspect, $R^{10}$ represents a radical selected from a linear or branched $C_{10}$ to $C_{22}$ alkyl group, a linear or branched $C_{10}$ to $C_{22}$ alkenyl group, an acyl group represented by $R^{11}C(O)$—, wherein $R^{11}$ is selected from a linear or branched $C_9$ to $C_{22}$ alkyl group, a linear or branched $C_9$ to $C_{22}$ alkenyl group. In one aspect, $M^+$ is selected from sodium, potassium, ammonium, and triethanolamine (TEA).

The amino acid surfactants can be derived from the alkylation and acylation of α-amino acids such as, for example, alanine, arginine, aspartic acid, glutamic acid, glycine, isoleucine, leucine, lysine, phenylalanine, serine, tyrosine, and valine. Representative N-acyl amino acid surfactants are, but not limited to the mono- and di-carboxylate salts (e.g., sodium, potassium, ammonium and TEA) of N-acylated glutamic acid, for example, sodium cocoyl glutamate, sodium lauroyl glutamate, sodium myristoyl glutamate, sodium palmitoyl glutamate, sodium stearoyl glutamate, disodium cocoyl glutamate, disodium stearoyl glutamate, potassium cocoyl glutamate, potassium lauroyl glutamate, and potassium myristoyl glutamate; the carboxylate salts (e.g., sodium, potassium, ammonium and TEA) of N-acylated alanine, for example, sodium cocoyl alaninate, and TEA lauroyl alaninate; the carboxylate salts (e.g., sodium, potassium, ammonium and TEA) of N-acylated glycine, for example, sodium cocoyl glycinate, and potassium cocoyl glycinate; the carboxylate salts (e.g., sodium, potassium, ammonium and TEA) of N-acylated sarcosine, for example, sodium lauroyl sarcosinate, sodium cocoyl sarcosinate, sodium myristoyl sarcosinate, sodium oleoyl sarcosinate, and ammonium lauroyl sarcosinate; and mixtures of the foregoing surfactants.

The betaines and sultaines useful in the composition are selected from alkyl betaines, alkylamino betaines, and alkylamido betaines, as well as the corresponding sulfobetaines (sultaines) represented by the formulas:

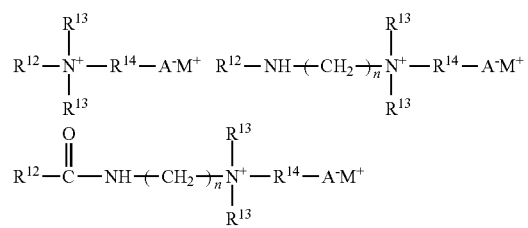

wherein $R^{12}$ is a $C_7$-$C_{22}$ alkyl or alkenyl group, each $R^{13}$ independently is a $C_1$-$C_4$ alkyl group, $R^{14}$ is a $C_1$-$C_5$ alkylene group or a hydroxy substituted $C_1$-$C_5$ alkylene group, n is an integer from 2 to 6, A is a carboxylate or sulfonate group, and M is a salt forming cation. In one aspect, $R^{12}$ is a $C_{11}$-$C_{18}$ alkyl group or a $C_{11}$-$C_{18}$ alkenyl group. In one aspect, $R^{13}$ is methyl. In one aspect, $R^{14}$ is methylene, ethylene or hydroxy propylene. In one aspect, n is 3. In a further aspect, M is selected from sodium, potassium, magnesium, ammonium, and mono-, di- and triethanolamine cations.

Examples of suitable betaines include lauryl betaine, coco betaine, oleyl betaine, cocohexadecyl dimethylbetaine, lauryl amidopropyl betaine, cocoamidopropyl betaine, and cocamidopropyl hydroxysultaine.

The alkylamphocarboxylates, such as the alkylamphoacetates and alkylamphopropionates (mono- and disubstituted carboxylates), can be represented by the formula:

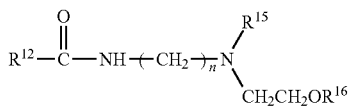

wherein $R^{12}$ is a $C_7$-$C_{22}$ alkyl or alkenyl group, $R^{15}$ is —$CH_2C(O)O^-M^+$, —$CH_2CH_2C(O)O^-M^+$, or —$CH_2CH(OH)CH_2SO_3^-M^+$, $R^{16}$ is a hydrogen or —$CH_2C(O)O^-M^+$, and M is a cation selected from sodium, potassium, magnesium, ammonium, and mono-, di- and triethanolamine.

Exemplary alkylamphocarboxylates include sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate.

The nonionic surfactant can be any of the nonionic surfactants known or previously used in the art of aqueous surfactant compositions. Suitable nonionic surfactants include, but are not limited to, aliphatic ($C_6$-$C_{18}$) primary or secondary linear or branched chain acids, alcohols or phenols; alkyl ethoxylates; alkyl phenol alkoxylates (especially ethoxylates and mixed ethoxy/propoxy moieties); block alkylene oxide condensates of alkyl phenols; alkylene oxide condensates of alkanols; and ethylene oxide/propylene oxide block copolymers. Other suitable nonionic surfactants include mono- or dialkyl alkanolamides; alkyl polyglucosides (APGs); sorbitan fatty acid esters; polyoxyethylene sorbitan fatty acid esters; polyoxyethylene sorbitol esters; polyoxyethylene acids, and polyoxyethylene alcohols. Other examples of suitable nonionic surfactants include coco mono- or diethanolamide, coco glucoside, decyl diglucoside, lauryl diglucoside, coco diglucoside, polysorbate 20, 40, 60, and 80, ethoxylated linear alcohols, cetearyl alcohol, lanolin alcohol, stearic acid, glyceryl stearate, PEG-100 stearate, laureth 7, and oleth 20.

In another embodiment, non-ionic surfactants include alkoxylated methyl glucosides such as, for example, methyl gluceth-10, methyl gluceth-20, PPG-10 methyl glucose ether, and PPG-20 methyl glucose ether, available from Lubrizol Advanced Materials, Inc., under the trade names, Glucam® E10, Glucam® E20, Glucam® P10, and Glucam® P20, respectively; and hydrophobically modified alkoxylated methyl glucosides, such as PEG 120 methyl glucose dioleate, PEG-120 methyl glucose trioleate, and PEG-20 methyl glucose sesquistearate, available from Lubrizol Advanced Materials, Inc., under the trade names, Glucamate® DOE-120, Glucamate™ LT, and Glucamate™ SSE-20, respectively, are also suitable. Other exemplary hydrophobically modified alkoxylated methyl glucosides are disclosed in U.S. Pat. Nos. 6,573,375 and 6,727,357.

Other surfactants which can be utilized in the composition are set forth in more detail in WO 99/21530, U.S. Pat. Nos. 3,929,678, 4,565,647, 5,720,964, and 5,858,948. In addition, suitable surfactants are also described in *McCutcheon's Emulsifiers and Detergents* (North American and International Editions, by Schwartz, Perry and Berch).

While the amounts of the surfactant utilized in a composition comprising the exemplary thermally-activated agent can vary widely depending on a desired application, the amounts which are often utilized generally range from 1 wt. % to 80 wt. %, on an actives basis. For example, the surfactant may be present in the composition, on an actives basis, at a total concentration of 0.001-20 wt. %, e.g., at least 0.1 wt. %.

3. Emulsifiers

Fatty alcohols and fatty acids, as well as their alkoxylates, the partial esters of polyglycerols, as well as the organosiloxanes are useful herein. The fatty alcohol may be obtained from natural sources and thus be a mixture of alcohols.

Emulsifiers, when employed in the exemplary compositions, may include fatty alcohols, such as or $C_{12}$-$C_{32}$ or $C_{12}$-$C_{22}$ fatty alcohols, alkoxylated alcohols, such as $C_{12}$-$C_{32}$ or $C_{12}$-$C_{22}$ alkoxylated alcohols, fatty acids, such as $C_{12}$-$C_{32}$ or $C_{12}$-$C_{22}$ fatty acids, alkoxylated fatty acids, such as $C_{12}$-$C_{32}$ or $C_{12}$-$C_{22}$ alkoxylated fatty acids (the alkoxylates each having 10 to 80 units of ethylene oxide, propylene oxide, and combinations of ethylene oxide/propylene oxide present in the molecule), $C_8$-$C_{22}$ alkyl polyglycosides (APGs), ethoxylated sterols (wherein the number of ethylene oxide units ranges from 2 to about 150), partial esters of polyglycerols, esters and partial esters of polyols having 2 to 6 carbon atoms, partial esters of polyglycerols, and organosiloxanes, and combinations thereof.

One example alcohol useful herein is cetearyl alcohol, which is a mixture of fatty alcohols, predominantly cetyl and stearyl alcohols. Since such fatty alcohols can serve as a rheology modifier in the composition, they are thus considered as rheology modifiers for purposes of defining the weights of components of the composition. Such fatty alcohols may also serve as emollients and/or conditioning agents.

Particularly suitable emulsifiers include polyoxyethylene ethers, such as ceteareth-n (where n represents the number of polyethylene units in the chain, such as from 2-100, e.g., 5-50), such as ceteareth 20.

Exemplary alkyl glucosides and oligoglycosides can be selected from octyl glucoside, decyl glucoside, lauryl glucoside, palmityl glucoside, isostearyl glucoside, stearyl glucoside, arachidyl glucoside and behenyl glucoside, and mixtures thereof.

Emulsifiers based on the esters and partial esters of polyols having 2 to 6 carbon atoms that are condensed with linear saturated and unsaturated fatty acids having 12 to 30 carbon atoms are, for example, the monoesters and diesters of glycerol or ethylene glycol or the monoesters of propylene glycol with saturated and unsaturated $C_{12}$-$C_{30}$ fatty acids.

The emulsifier may be suitably present at 0.01-20 wt. % of the composition, such as at least 0.1 wt. %, e.g., up to 5 wt. %, which for purposes of computing amounts present in the composition, excludes those listed above as rheology modifiers.

4. Conditioning Agents

Exemplary conditioning agents include polyquaternium-n (polycationic polymers including a quaternary ammonium center in the polymer), wherein n is from 1-47, each n designating a specific polymer, such as polyquaternium 37, and amine-functionalized silicones, such as amodimethicone. Another suitable conditioning agent is hydrolyzed keratin.

Such conditioning agents may be present at from 0.01-20 wt. % of the composition, such as at least 0.1 wt. %, e.g., up to 5 wt. %.

5. Humectants

Humectants suitable for use in the composition of the invention include, but are not limited to, glycerol, polyglycerols, sorbitol, propane-1,2-diol (propylene glycol), butane-1,2,3-triol, polyethylene glycols, glucose, mannitol, xyliyol, and mixtures thereof.

Such humectants may be present at from 0.01-20 wt. % of the composition, such as at least 0.1 wt. %, or at least 1 wt. %, e.g., up to 8 wt. %, or up to 5 wt. %.

6. Preservatives

In one aspect, any preservative suitable for use in personal care can be used in the composition for straightening hair. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds as disclosed above (e.g., Polyquaternium-1).

In another aspect, acid based preservatives are useful in the exemplary compositions. The use of acid based preservatives facilitates the formulation of products in the low pH range. Lowering the pH of a formulation inherently provides an inhospitable environment for microbial growth in addition to being suited to the straightening process. Moreover, formulating at low pH enhances the efficacy of acid based preservatives, and affords a personal care product which maintains an acidic pH balance on the skin. Any acid based preservative that is useful in personal care products can be used in the exemplary compositions. In one aspect the acid preservative is a carboxylic acid compound represented by the formula: $R^3C(O)OH$, wherein $R^3$ represents hydrogen, a saturated and unsaturated hydrocarbyl group containing 1 to 8 carbon atoms or $C_6$ to $C_{10}$ aryl. In another aspect, $R^3$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, and benzoic acid, and mixtures thereof.

In another aspect, suitable acids include but are not limited to, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and mixtures thereof.

Salts of the foregoing acids are also useful as long as they retain efficacy at low pH values. Suitable salts include the alkali metal (e.g., sodium, potassium, calcium) and ammonium salts of the acids enumerated above.

The acid based preservatives and/or their salts can be used alone or in combination with non-acidic preservatives typically employed in personal care, home care, health care, and institutional and industrial care products.

The preservatives may comprise from 0.01 wt. % to 3.0 wt. % in one aspect, or from 0.1 wt. % to 1 wt. %, or from 0.3 wt. % to 1 wt. %, of the total weight of the hair straightening composition.

7. Chelating Agents

Chelating agents can be employed to stabilize the composition against the deleterious effects of metal ions. When utilized, suitable chelating agents include EDTA (ethylene diamine tetraacetic acid) and salts thereof such as disodium EDTA, citric acid and salts thereof, cyclodextrins, and the like, and mixtures thereof.

Such suitable chelating agents can comprise 0.001 wt. % to 3 wt. %, such as 0.01 wt. % to 2 wt. %, or 0.01 wt. % to 1 wt. % of the total weight of the hair straightening composition.

8. Propellants

Where desired, any known aerosol propellant can be utilized to deliver the hair straightening compositions onto the surface of the hair to be straightened. Exemplary propellants include lower boiling hydrocarbons such as $C_3$-$C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane, and compressed gases, such as air and carbon dioxide.

In one aspect, these compositions can contain from 0.1 wt. % to 60 wt. %, or 0.5 to 35 wt. % propellant, based on the total weight of the composition.

9. Fragrances and Perfumes

Fragrance and perfume components that may be used in the exemplary composition include natural and synthetic fragrances, perfumes, scents, and essences and any other substances which emit a fragrance. As the natural fragrances, there are those of vegetable origin, such as oil extracts from flowers (e.g., lily, lavender, rose, jasmine, neroli, ylang-ylang), stems and leaves (geranium, patchouli, petitgrain, peppermint), fruits (aniseed, coriander, fennel, needle juniper), fruit skin (bergamot, lemon, orange), roots (mace, angelica, celery, cardamom, costus, iris, sweet flag), woods (pine tree, sandalwood, guaiacum wood, cedar, rosewood, cinnamon), herbs and grasses (tarragon, lemongrass, sage, thyme), needles and twigs (spruce, pine, European red pine, stone pine), and resins and balsam (galbanum, elemi, benzoin, myrrh, frankincense, opopanax), and those of animal origin, such as musk, civet, castoreum, ambergris, or the like, and mixtures thereof.

Examples of synthetic fragrances and perfumes are the aromatic esters, ethers, aldehydes, ketones, alcohols, and hydrocarbons including benzyl acetate, phenoxyethyl isobutylate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styralyl propionate, and benzyl salicylate; benzylethyl ether; straight chain alkanols having 8 to 18 carbon atoms, citral, citronellal, citronellyloxyaldehyde, cyclamen aldehyde, hydroxycitronellal, lilial, and bougeonal; ionone compounds, α-isomethyl ionone, and methyl cedryl ketone; anethole, citronellol, eugenol, isoeugenol, geraniol, lavandulol, nerolidol, linalool, phenylethyl alcohol, and terpineol, alpha-pinene, terpenes (e.g., limonene), and balsams, and mixtures thereof.

10. Botanicals

Suitable botanical agents useful herein may include, for example, extracts from *Echinacea* (e.g., sp. *angustifolia, purpurea, pallida*), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanical extracts may also include, for example, chlorogenic acid, glutathione, glycrrhizin, neohesperidin, quercetin, rutin, morin, myricetin, absinthe, and chamomile.

11. Hair Fixing Agents

Hair fixing agents may be included in addition to the exemplary thermally-activated agent, including polymer fixatives such as 3-aminopropyl methyl, dimethyl, reaction products of silicones and siloxanes with 2-ethyl-4,5-dihydrooxazole homopolymer, ethyl sulfates, such as Polysilicone-9, and film-forming polymers such as polyacrylic acid and sodium polyacrylate polymer fixatives, such as Fixate™ RSP available from Lubrizol Corp.

The hair fixing agent may be present in the composition at from 0.001 wt. % to 20 wt. %, such as at least 0.1 wt. %, or up to 5 wt. %.

12. Emollients

Emollients, other than those listed above, may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

An example emollient useful herein is diisopropyl adipate.

13. Buffer Agents

Buffering agents can be used in the exemplary compositions. Suitable buffering agents include alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

Other auxiliary components useful herein may include UV-absorbers, such as benzophenone-4.

The composition may exclude certain components, such as hair coloring agents (hair dyes), peptides, sulfites, bisulfites, and cyclic mercapto compounds which are not of benefit in simply a hair-straightening application.

Example Cream Formulations

As an example, cream formulations may be formulated as shown in Table 1:

TABLE 1

Example Compositions

| Component | Example 1 Wt. % actives | Example 2 Wt. % actives |
| --- | --- | --- |
| Thermally-activated agent | 5-95, or 5-60 | 15-50 |
| Rheology modifier | 0-20 | 1-10 |
| Cationic surfactant | 0-20 | 1-5 |
| pH modifier (or in an amount sufficient to provide a pH of up to 8.5) | 0.01-10 | 0.02-5 |

TABLE 1-continued

Example Compositions

| Component | Example 1 Wt. % actives | Example 2 Wt. % actives |
| --- | --- | --- |
| Preservative | 0-2 | 0.01-1 |
| Organic solvent | 0-50 | 0.2-30 |
| Other components | 0-20 | 0-10 |
| Water | q.s. to 100% | q.s. to 100% |

As will be appreciated, compositions can be formed by combining ranges from Examples 1 and 2. Additionally, the selected process, such as contact time and heating temperature, may also influence the selection of the composition components and their amounts, as demonstrated by the examples below.

The semi-permanent hair straightening composition can be provided and dispensed from suitable package forms, such as pressurized and non-pressurized containers, such as cans, bottles, packets, ampoules, jars, tubes, and the like. Spray compositions can be dispensed from finger-actuated pump devices, either as pressurized aerosol sprays, mousses, spritzes, and foams containing propellant, or as non-pressurized, mechanically propelled sprays and foams.

The exemplary composition can be utilized on hair to impart an excellent straightening effect by using heat. The treatment method includes first coating the hair with the composition. This may be performed with any suitable applicator, such as a brush, comb, sponge, pad, cloth, fingers e.g., while wearing gloves, to coat the fibers with the composition. The composition is left in contact with the hair for a sufficient time period for the thermally-activated agent to penetrate into the fibers, such as several minutes, e.g., at least five or at least ten minutes, or at least twenty minutes, or at least thirty minutes, and up to sixty, or up to forty, or up to thirty minutes. The optimum contacting time may vary, depending on factors such as the concentration of thermally-activated agent and the temperature of the heating device used to contact the hair in the heating stage.

The heat may be applied with a heating device which provides a temperature sufficient to activate the thermally-activated agent of Structure (1), such as a temperature of at least 185° C., or at least 190° C., or at least 200° C., or at least 205° C. or at least or about 210° C. and up to 230° C. or up to 225° C., or up to 220° C. The heating device is retained in contact with the hair for sufficient time to effect the desired modification, such as an increase in length of a hair tress of at least 5%, or at least 10%. The time depends on a number of factors such as the moisture content of the hair, temperature of the heating device, concentration of the thermally-activated agent and so forth, but is generally at least 10 seconds, or at least 1 or 2 minutes, in total, for each centimeter length of hair. Example heating devices include flat or round irons, microwave generators, sources of infrared radiation, and the like. In the case of flat or round iron, for example, the heating device has at least one surface (which is brought into contact with the fibers) which is raised, e.g., with an electric power source, to a surface temperature of at least 180° C., or at least 190° C., or at least 200° C., or at least 205° C. or at least or about 210° C. and up to 230° C. or up to 225° C., or up to 220° C.

The temperature of the hair tress can be measured, for example, with a thermocouple positioned within the hair tress and may reach a temperature of at least 150° C. or at least 170° C. during the heating with the heating device.

Optionally, the hair can be dried to some extent after treatment with the straightening composition and prior to application of heat to raise the temperature of the keratin fibers and/or to avoid substantial release of steam during the heating stage. For example, partial drying may be achieved by blow drying with a hairdryer, a drying hood at a temperature of about 100° C., by free drying, wiping with a towel, etc. For example, the moisture content of the composition may be reduced to 10 wt. % or less, such as about 2 wt. %, prior to applying heat with the heating device. In general, the drying is performed to remove solvent while retaining at least a portion, or all, of the applied thermally-activated agent on the hair. For this reason also, the hair is not rinsed (e.g., with water or other aqueous solution) between the applying and the heating stages in the exemplary embodiment.

The end of the iron that comes into contact with the hair generally has two flat surfaces. These two flat surfaces may be metallic or ceramic. They may be smooth or notched. The application of the iron may be performed by successive touches separated by a few seconds, or by gradual moving or sliding along locks, etc. The application of the iron in the exemplary process is performed by continuous movement from the root to the end, in one or more passes, such as at least five passes.

Without wishing to be bound by any particular theory, it is suggested that the hot flat iron softens hard α-keratins and straightens the hair fiber and synergistically, the heat imparted by the flat iron activates a reaction (e.g., a cross-linking or other modification reaction) between the cyclic carbonates (or other thermally-activated agent according to Structure (I)) and the amine groups of the hair fibers, possibly resulting in N, N'-disubstituted urea linkages. This results in a fixation of the newly formed shape.

Results of tests suggest that ethylene carbonate, among others, such as in an aqueous solution, can readily penetrate the hair fibers and react with hard proteinaceous materials via a flat iron at a temperature higher than 185° C. or such as about 210° C. The curly hair-tresses used in the tests, once straightened, can withstand up to 50 shampoo-wash-cycles. The straightened hair-tresses look shiny and feel smooth and silky without malodor. Propylene carbonate and glycerol carbonate were less effective, when used alone under the same conditions, but can be used in combination with other thermally-activated agents of Structure (I) or other cross-linking agents.

Alkylene carbonates, in particular, ethylene carbonate, have been shown to be effective protein modifier or cross-linking agents imparting the ease and effectiveness of desired reactions acting upon keratin peptides. In brief, applying an aqueous solution containing ethylene carbonate to hair followed by a hot flat iron treatment (e.g., at 210° C.) can effectively modify its shape as desired and that this shape can last for days to weeks (e.g., 50 shampoos or equivalent to about 4 months) without returning to its original curly state. This compares very favorably with formaldehyde based formulations.

By way of example, the process provides some or all of the following attributes:
1. Activated via flatiron to create straight, smooth, sleek hair
2. Retains style for at least 24 shampoo-washes and up to 8 or 12 weeks (for a consumer using 3 shampoo-washes/week), and can be up to 50 shampoos or equivalent to about 4 months, or longer
3. Resistant to high humidity
4. Less heat damage to the hair than existing, formaldehyde-based hair straightening compositions
5. Low or no volatile organic compounds (VOCs)
6. Formaldehyde-free
7. Applicable to all hair-types, including natural and chemically-treated hair
8. Suitable for home use as well as salon application Without intending to limit the scope of the exemplary embodiment, the following examples demonstrate the effectiveness of example compositions.

EXAMPLES

In the following examples, the hair type and curliness is based on the definition published by L'Oréal (Roland de la Mettrie, et al. "Shape Variability and Classification of Human Hair: A Worldwide Approach," Human Biology, June 2007). This assigns a number to the hair from I-VIII, with I being the straightest and VIII representing dense, very curly hair. In general, the samples used herein were curly, classed as type 4-5. After thermal straightening, the hair-tress typically becomes type I. However, the hair relaxes on washing. If, after 3-shampoo-wash-cycle, the hair-tress relaxes to type 3-4, this can be considered as inefficiently straightened (relaxed).

To simulate human hair on the head, curly Brazilian hair tresses were obtained from International Hair Importer and Product Inc. Each single hair-tress is about 2.5 g in weight and has approximate dimensions of 20 cm in length and 10 cm in width at the widest point. The tresses are each clamped at the root end.

Prior to use, each virgin dark brown curly hair-tress was shampooed by using a commercial clarifying shampoo (VO5™ or Suave™ shampoo) by gently massaging for 30 seconds followed by rinsing for 60 seconds with running warm water (35-38° C.). Each washed hair-tress is then dried at room temperature under 30-50% RH conditions.

Two different application methods were evaluated:
1. Solution-Dipping

This method is used primarily to screen and select candidate molecules as possible thermally-activated agents. Typically, a solution of the candidate molecule is prepared in a suitable solvent system. The hair-tress is immersed completely in the solution with controlled concentration of candidate thermally-activated agent, pH, temperature and soaking time, such as for up to 60 minutes. Then, the hair-tress is removed from the solution, excess amount of material squeezed out, and the tress is blow-dried to at least 95% dryness before thermal straightening.

2. Cream Chassis

Candidate thermally-activated agents which perform well on the solution dip method are incorporated in a cationic emulsion or cream chassis system at different levels and pH, as shown in Table 2:

TABLE 2

Cream Chassis Formulas

| Component | Function | Amount of active, wt. % |
|---|---|---|
| thermally-activated agent, e.g., EC | Thermally-activated hair straightening agent | Different amounts |
| Paraffinum Liquidum | Rheology modifier and emollient | 3.00 |
| Cetearyl alcohol | Rheology modifier and conditioning agent | 2.50 |

TABLE 2-continued

Cream Chassis Formulas

| Component | Function | Amount of active, wt. % |
|---|---|---|
| Diisopropyl adipate | Emollient | 1.50 |
| Cetrimonium chloride (50 wt. % active) | Surfactant/Conditioning agent | 1.40 |
| Ceteareth-20 | Emulsifier | Different amounts |
| Citric acid (10 wt. % active) | pH modifier | 0.20 |
| NaOH (18 wt. % active) | pH modifier | Different amounts, to achieve desired pH |
| Methylchloro-isothiazolinone (and) methylisothiazolinone (preservative) | Preservative | 0.05 |
| Water | Solvent/diluent for thermally-activated agent | q.s. to 100% |

The product is applied on a cleaned curly hair-tress and allowed to rest according to the protocol. After the controlled application time, the hair-tress is blow-dried to at least 95% of dryness before thermal straightening.

For thermal straightening by flatiron, a commercial flat iron, sold under the tradename Nano Titanium™ by BaByliss PRO was used. The protocol used was the following:
1. The flat iron is set at targeted temperature (≤210° C.).
2. The heated flat iron is drawn from the top to the bottom of the tress in approximately 12 seconds.
3. The thermal process is repeated for the desired straightening level (e.g., 10-12 passes at 210° C.).

After the thermal straightening treatment, the hair-tress is allowed to cool down to the room temperature.

Wash-Fastness:

The shampoo-wash-fastness is carried out by applying shampoo (VO5 or Suave shampoo) on the hair-tress which is massaged for 30 seconds followed by rinsing for 60 seconds with running warm water (32-35° C.). The washed hair-tress is then dried at 23° C. and 50% RH. Consecutive shampoo-wash-cycles are carried out without the drying step.

Humidity Resistance:

Thermal-straightened hair-tresses after a certain numbers of shampoo-wash are dried before being placed in a humidity chamber with controlled temperature and % RH.

Two methods are used to evaluate the thermal straightening efficiency:
1. Visual Evaluation: the treated hair-tresses are visually examined and compared against an untreated hair-tress. A comparison is also made against a control which is thermally treated only.
2. Image Analysis: the method can be used to quantify the curly hair-tress thermal straightening efficiency for different treatments. Measurements of tress length and width at half-length can be made with this method.

In the following initial screening test, the examination of thermally straightened hair-tresses is performed by visually examining a tress which has been treated in a solution containing up to 30 wt. % of a candidate thermally-activated agent for 45 minutes, flat-ironed at 210° C. (10×12 seconds). After three consecutive wash cycles, if the dried hair-tress (23° C. and 50% RH) becomes curly, this material is considered not effective, i.e. not worth a further evaluation in a cream formulation.

Thermal Breakage Quantification:

Thermal straightened hair-tresses after a certain number of shampoo-washes are dried before being placed in the humidity chamber with controlled temperature and % RH. Then a single hair-tress is combed with a comb with a constant force from the root to the tip, and the stroke is repeated for 100 times. When completed, hair fiber fragments that have broken from the tress are counted for comparison.

Results

Nine groups of small molecules are being compared in the first evaluation (solution-based):
1) Cyclic Carbonates:
   a. ethylene carbonate (EC),
   b. propylene carbonate (PC),
   c. glycerin carbonate (GC),
   d. trimethylene carbonate (TC);
2) Linear Carbonates:
   a. dimethyl carbonate,
   b. diethyl carbonate;
3) Cyclic Lactones:
   a. γ-valerolactone,
   b. δ-valerolactone,
   c. ε-caprolactone,
   d. pantolactone;
4) Cyclic Lactams:
   a. γ-butyrolactam,
   b. 1-methyl-2-pyrrolidone,
   c. δ-valerolactam,
   d. ε-caprolactam;
5) Other Heterocyclic Molecules:
   a. 2-oxazolidinone (O),
   b. 2-imidazolidinone;
6) Sulfones:
   a. dimethyl sulfone,
   b. sulfolane (2,3,4,5-tetrahydrothiophene-1,1-dioxide)
7) Ureas
   a. Urea (U)
   b. Ethylene Urea (EU)
8) Glyoxylic Acid (GA)
9) Formaldehyde (F)

Selected candidate molecules are further evaluated using cream formulations. Tables 3-5 show some of the results obtained for the cream formulations where the following abbreviations are used:

Initial Hair Condition:
   NR=newly received (virgin hair)
   PU=previously used (used in other evaluations, leading to some damage of the hair)

Shampoo Treatment:
   S=shampoo right after straightening
   L=left overnight (12 hours) prior to first wash Visual observations are made at the completion of the treatment protocol.

TABLE 3

Results for cream formulations with ethylene carbonate

| Ex. | EC, wt. % | pH | Soak Time, mins | Iron Temp. ° C. | Passes | Wash-Cycles | Hair Tresses | Observation |
|---|---|---|---|---|---|---|---|---|
| 1 | 0 | — | — | 227 | 10 | 3 | NR-curly | curly (control) |
| 2 | 15 | 6.7 | 35 | 208 | 12 | 6 | PU-curly | Straight- |
| 3 | 15 | 6.4 | 35 | 208 | 12 | 6 | PU-curly | Straight |
| 4 | 15 | 6.4 | 35 | 208 | 12 | 6 | PU-curly | Straight |
| 5 | 15 | 5.5 | 30 | 206 | 10 | 3 | Hard curly | curly |

TABLE 3-continued

Results for cream formulations with ethylene carbonate

| Ex. | EC, wt. % | pH | Soak Time, mins | Iron Temp. ° C. | Passes | Wash-Cycles | Hair Tresses | Observation |
|---|---|---|---|---|---|---|---|---|
| | | | | | | | | (hard-hair) |
| 6 | 15 | 6.7 | 30 | 208 | 10 | 3 L | NR-curly | curly |
| 7 | 15 | 6.7 | 30 | 208 | 10 | 3 | NR curly | less curly |
| 8 | 15 | 6.7 | 45 | 208 | 10 | 3 L | NR-curly | curly |
| 9 | 15 | 6.5 | 60 | 208 | 12 | 50 | curly | straight |
| 10 | 15 | 6.5 | 60 | 208 | 10 | 6 | NR-curly | straight |
| 11 | 15 | 6.5 | 90 | 208 | 10 | 6 | NR-curly | straight |
| 12 | 30 | 6.7 | 30 | 169 | 10 | 3 | NR-curly | curly |
| 13 | 30 | 6.6 | 30 | 170 | 10 | 6 | PU-curly | curly |
| 14 | 30 | 6.7 | 30 | 189 | 10 | 3 | NR-curly | curly |
| 15 | 30 | 6.6 | 30 | 190 | 10 | 6 | PU-curly | straight |
| 16 | 30 | 6.6 | 30 | 210 | 10 | 6 | PU-curly | straight |
| 17 | 30 | 6.7 | 30 | 209 | 10 | 3 | NR-curly | less curly |
| 18 | 30 | 6.7 | 30 | 208 | 10 | 3 L | NR-curly | less curly |
| 19 | 30 | 6.7 | 30 | 208 | 10 | 3 | NR-curly | less curly |
| 20 | 30 | 6.7 | 30 | 207 | 10 | 3 | NR-curly | less curly |
| 21 | 30 | 6.7 | 45 | 208 | 10 | 50 L | NR-curly | straight |
| 22 | 30 | 6.7 | 45 | 208 | 10 | 50 L | NR-curly | straight |
| 23 | 30 | 6.7 | 45 | 208 | 10 | 50 L | NR-curly | straight |
| 24 | 30 | 6.7 | 45 | 208 | 10 | 50 | curly hair | straight |
| 25 | 30 | 6.7 | 45 | 208 | 10 | 50 | NR-curly | straight |
| 26 | 30 | 6.7 | 45 | 208 | 10 | 50 | NR-curly | straight |
| 27 | 30 | 6.7 | 60 | 208 | 10 | 50 | NR-curly | straight |
| 28 | 30 | 6.7 | 30 | 226 | 10 | 12 | NR-curly | straight |
| 29 | 30 | 6.7 | 30 | 226 | 10 | 3 | NR-curly | straight |
| 30 | 30 | 6.7 | 45 | 228 | 10 | 3 | NR-curly | straight |
| 31 | 30 | 6.7 | 45 | 228 | 10 | 12 | NR-curly | straight |

TABLE 4

Results for cream formulations with Ethylene Carbonate + Propylene Carbonate

| Ex. | EC+PC, wt. % | EC:PC | pH | Soak Time, mins | Iron Temp. ° C. | Passes | Wash-Cycles | Hair-Tresses | Observation |
|---|---|---|---|---|---|---|---|---|---|
| 32 | 30 | 90/10 | 6.48 | 45 | 208 | 10 | 24 | NR-curly | straight |
| 33 | 30 | 80/20 | 6.18 | 45 | 208 | 10 | 24 | NR-curly | straight |
| 34 | 30 | 75/25 | 6.15 | 45 | 208 | 10 | 24 | NR-curly | straight |
| 35 | 30 | 50/50 | 6.16 | 45 | 208 | 10 | 24 | NR-curly | straight |

TABLE 5

Results for cream formulations with Propylene Carbonate

| Ex. | PC, wt. % | pH initial | pH final | Soak Time, mins | Iron Temp., ° C. | Passes | Wash-Cycles | Hair-Tresses | Observation |
|---|---|---|---|---|---|---|---|---|---|
| 36 | 15 | 6.02 | 6.74 | 30 | 210 | 10 | 3 | PU-curly | Curly |
| 37 | 15 | 6.40 | 6.30 | 30 | 210 | 10 | 3 | PU-curly | Curly |
| 39 | 15 | 8.51 | 8.11 | 30 | 210 | 10 | 3 | PU-curly | curly |
| 40 | 15 | 9.64 | 8.97 | 30 | 210 | 10 | 3 | PU-curly | curly |
| 41 | 30 | 6.50 | 6.50 | 30 | 208 | 10 | 3 | NR-curly | curly |
| 42 | 30 | 6.50 | 6.50 | 60 | 208 | 10 | 3 | NR-curly | curly |
| 43 | 50 | 6.50 | 6.50 | 30 | 208 | 10 | 3 | NR-curly | curly |
| 44 | 50 | 6.50 | 6.50 | 60 | 208 | 10 | 3 | NR-curly | curly |

Examples 21-27 and 32-36 had almost no malodor, and were smooth, sleek and healthy looking. Examples 28-31, straightened at temperatures above 225° C. showed some damage, presumably due to the higher temperature.

The results demonstrate that the straightening can be achieved by selection of soaking time, flat iron temperature, and concentration of thermally-activated agents. For example increased soaking time can compensate for lower iron temperature and/or concentration.

Imaging Analysis

An imaging analysis method was developed to evaluate the thermally straightening efficiency of exemplary thermally-activated agents (ethylene carbonate, trimethylene carbonate, and oxazolidinone) and other small molecules, such as formaldehyde, urea, and glyoxylic acid.

As for other tests, a curly hair-tress was completely immersed in an aqueous solution of a selected one of the small molecules and soaked for 45 minutes. Each solution contained an equimolar amount of the selected small molecule. The hair-tress was then removed from the solution, excess water was squeezed out manually, and the hair dried by a blower dryer to the desired dryness before thermal straightening, as described above.

The imaging analysis method was used to measure the total length and width of the hair-tress before and after the thermal straightening process, and after each shampoo-wash-cycle. More specifically, photographs of hair tresses or bundles of hair tresses were taken against a solid color background with a tripod-mounted digital camera. Illumination was selected to minimize shadows which could affect measurements. The tress was hung from a spindle that enabled the tress to be rotated 90 degrees so that pictures could be taken from four different angles, providing a full view of the tress, with a ruler mounted close to the tress as a scale.

The National Institutes for Health's Image J software program was used for image processing and analysis. Table 6 shows the length, and width (at half-length). The curly hair-tress has a contour length of 20 cm, and the top glued part is 2.0 cm wide and is about 0.4 cm of length. Therefore, the effective hair-tress contour length is 19.6 cm.

The imaging analysis data thus shows that ethylene carbonate (EC) and trimethylene carbonate (TC) behave similarly to formaldehyde (F) and glyoxylic acid (GA), yet without the potential hazards that these small molecules pose. Oxazolidinone (O) gives better straightening results than urea (U) and ethylene urea (EU). Urea and ethylene urea relax the curly hair-tress to some degree. The ranking of the molecules for semi-permanent thermal straightening efficiency from this data is:

GA≈EC≈F≥TC>O>EU>U

TABLE 6

Thermal straightening efficacy analyzed by imaging analysis method

| Small Molecule | U | EU | O | TC | F | EC | GA |
|---|---|---|---|---|---|---|---|
| Length$_{max}$ (cm) | | | | | | | |
| Control | 15.9 | 16.0 | 16.1 | 16.5 | 16.0 | 16.8 | 16.1 |
| Thermally-treated | 19.6 | 19.4 | 19.3 | 19.8 | 19.4 | 19.4 | 19.5 |
| Av.: 1-24 shampoos | 18.2 ± 0.2 | 18.2 ± 0.2 | 18.4 ± 0.1 | 19.0 ± 0.1 | 19.1 ± 0.1 | 19.4 ± 0.1 | 19.2 ± 0.3 |
| Front: Width$_{1/2}$ (cm) | | | | | | | |
| Control | 5.3 | 5.1 | 5.5 | 5.9 | 5.2 | 5.4 | 4.7 |
| Thermally-treated | 3.6 | 3.2 | 3.3 | 3.1 | 3.5 | 3.6 | 2.8 |
| Av.: 1-24 shampoos | 5.8 ± 0.2 | 4.1 ± 0.2 | 3.9 ± 0.2 | 3.3 ± 0.1 | 3.3 ± 0.3 | 2.6 ± 0.1 | 2.5 ± 0.5 |
| Side: Width$_{1/2}$ (cm) | | | | | | | |
| Control | 3.0 | 2.9 | 4.3 | 4.4 | 3.0 | 4.4 | 3.0 |
| Thermally-treated | 2.0 | 1.6 | 1.7 | 0.8 | 1.4 | 0.9 | 1.2 |
| Average: 1-24 shampoos | 4.0 ± 0.4 | 2.6 ± 0.1 | 2.7 ± 0.2 | 1.9 ± 0.2 | 1.8 ± 0.3 | 1.5 ± 0.1 | 1.4 ± 0.2 |

Formulation Testing

In the following tests, ethylene carbonate or trimethylene carbonate was admixed with various commercial hair treatment products and the mixtures were evaluated for straightening efficiency.

The ethylene carbonate or trimethylene carbonate was melted at about 40° C. and the resulting liquid was quickly added to the selected commercial product and mixed until homogenous. In the following tests, the EC or TC active level of the mixture was 15 wt. %-30 wt. %.

After subjecting the curly hair-tress to the same thermal hair straightening process as described above, as shown in Table 7, similar straightening results were obtained to the ones obtained to the tests described above for simple aqueous solutions, suggesting that the hair straightening composition can be formulated with a variety of conventional hair treatment auxiliaries without deleterious effect. It may be noted that none of the commercial products used in the tests provided a long-term semi-permanent hair straightening effect when used alone, although some provided an initial straightening effect that was lost after a single wash, based on a visual examination.

TABLE 7

Commercial Product Mixes

| | Wt. % thermally activated agent | Straightening efficiency (No. of shampoo wash cycles |
|---|---|---|
| Commercial A (gel formulation, fixative) | 15% EC | ≥30 |
| Commercial B (frizz reducer) | 25% TC | ≥30 |
| Commercial C (cream frizz reducer) | 20% EC | ≥30 |
| Commercial D (cream styling fixative formulation) | 30% EC | ≥30 |
| Commercial E (cream straightening formulation) | 30% EC | ≥30 |
| Commercial F (keratin-containing straightening formulation) | 30% EC | ≥30 |

The results show the compatibility of ethylene carbonate and trimethylene carbonate with a wide range of compositions.

Example Compositions

Table 8 shows an example spray formulation.

TABLE 8

Hair Frizz-Reducing Spray

| Ingredient | Function | Weight % Actives |
|---|---|---|
| Ethanol | solvent | 20.0 |
| Ethylene carbonate | thermally-activated agent | 10.0 |
| Polysilicone-9 | hair fixing agent | 0.7 |
| Cetrimonium chloride | surfactant, conditioning agent | 0.3 |
| Propylene glycol | humectant | 2.0 |
| Benzyl alcohol | solvent | 1.0 |
| Malic acid | pH modifier | 3.0 |
| Lactic acid | pH modifier | 2.0 |
| Sodium hydroxide | pH modifier | q.s. to pH = 4.5 |
| Hydrolyzed keratin | conditioning agent | q.s. |
| Benzophenone-4 | UV absorber | q.s. |
| Fragrance | fragrance | q.s. |
| Disodium EDTA | chelating agent | q.s. |
| Methylchloro-isothiazolinone (and) Methylisothiazolinone | preservative | q.s. |
| Water | solvent | q.s. to 100 |

Table 9 shows an example cream formulation.

TABLE 9

Hair Volume Control Cream

| Ingredient | Function | Weight % Actives |
|---|---|---|
| Ethylene carbonate | Thermally-activated agent | 15.0 |
| Paraffinum Liquidum | Rheology modifier, emollient | 3.0 |
| Cetearyl alcohol | Conditioning agent | 2.5 |
| Diisopropyl adipate | Emulsifier | 1.5 |
| Cetrimonium chloride (50%) | Conditioning agent | 2.8 |
| Ceteareth-20 | Emulsifier | 0.5 |
| Fragrance | Fragrance | 0.5 |
| Citric Acid (10%) | pH modifier | 0.2 |
| NaOH (18%) | pH modifier | q.s. to pH = 5.0-6.0 |
| Methylchloro-isothiazolinone (and) methylisothiazolinone | Preservative | 0.05 |
| Water | Solvent for EC | q.s. to 100 |

Table 10 shows another example formulation.

TABLE 10

Hair Straightening System

| Ingredient | Function | Weight % |
|---|---|---|
| Ethylene carbonate | Thermally-activated agent | 30.0 |
| Paraffinum liquidum | Emollient | 3.0 |
| Cetearyl alcohol | Conditioning agent | 2.5 |
| Diisopropyl adipate | Emulsifier | 1.5 |
| Behentrimonium chloride | Conditioning agent | 1.5 |
| Ceteareth-20 | Emulsifier | 0.5 |
| Citric Acid (10%) | pH modifier | 0.2 |
| NaOH (18%) | pH modifier | q.s. to pH = 4.5-6.5 |
| Fragrance | Fragrance | 0.5 |
| Methylchloro-isothiazolinone (and) Methylisothiazolinone | Preservative | 0.05 |
| Water | Solvent for EC | q.s. to 100 |

Table 11 shows another example formulation.

TABLE 11

Hair Straightening with Shine

| Ingredient | Function | Weight % |
|---|---|---|
| Ethylene carbonate | Thermally-activated agent | 30.0 |
| Amodimethicone | Conditioning agent | 3.0 |
| Cetearyl alcohol | Conditioning agent | 2.5 |
| Trideceth-5 | Emulsifier | 0.5 |
| Polyquaternium-37 | Conditioning agent | 0.8 |
| Phenoxyethanol | Preservative | 0.5 |
| Propylene Glycol | Humactant | 1.5 |
| Dicaprylate/Dicaprate | Emollient | 1.0 |
| Phenyl trimethicone | Conditioning agent | 1.0 |
| Cetyl Hydroxyethylcellulose | Rheology modifier | 0.5 |
| Benzyl alcohol | Solvent | 0.5 |
| Polysorbate 60 | Emulsifier | 0.3 |
| Citric acid (10%) | pH modifier | 0.2 |
| NaOH (18%) | pH modifier | q.s. to pH = 5.0-6.0 |
| Fragrance | Fragrance | 0.5 |
| Methylchloro-isothiazolinone (and) Methylisothiazolinone | Preservative | 0.05 |
| Water | Solvent | q.s. to 100 |

Table 12 shows an example gel formulation.

TABLE 12

Hair Straightening Gel

| Ingredient | Function | Weight % |
|---|---|---|
| Ethylene carbonate | Thermally-activated agent | 20.0 |
| Disodium EDTA | Chelating agent | 0.05 |
| Glycerin | Emollient | 2.0 |
| Carbopol ® 940 | Rheology modifier | 0.2 |
| Fixate ™ RSP (polyacrylic acid and sodium polyacrylate polymer fixative) | Hair fixing agent | 0.6 |
| Triethanolamine (99%) | pH modifier | q.s. to pH = 5.0 |
| Benzyl alcohol | Organic solvent | 0.05 |
| Fragrance | Fragrance | q.s. |
| Methylchloroisothiazolinone (and) Methylisothiazolinone | Preservative | q.s. |
| Water | Solvent | q.s. to 100 |

Each of the documents referred to above is incorporated herein by reference in its entirety. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements. As used herein, the expression "consisting essentially of" permits the inclusion of substances that do not materially affect the basic and novel characteristics of the composition under consideration. As used herein any member of a genus (or list) may be excluded from the claims.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A process for straightening hair comprising;
   coating hair fibers with a composition comprising ethylene carbonate; and
   contacting the coated hair fibers with a heating device at a temperature of at least 185° C. for at least 5 passes of continuous movement of said heating device from the root of the hair to the end to modify the hair fibers,
   and wherein said composition is free of cyclic mercapto-group, thiols group and sulfite group containing compounds.

2. The method of claim 1, wherein the composition further comprises a solvent.

3. The process of claim 2, wherein the solvent is selected from water, $C_1$-$C_{12}$ alcohols, and combinations thereof.

4. The process of claim 3, wherein the solvent is selected from $C_1$-$C_{10}$ aliphatic and aromatic alcohols.

5. The process of claim 4, wherein the solvent is selected from ethylene glycol, propylene glycol, glycerin, butylene glycol, hexylene glycol, ethanol, propanol, isopropanol, hexanol, benzyl alcohol, cyclohexanol, and mixtures thereof.

6. The process of claim 2, wherein the solvent is selected from natural and synthetic oils and waxes.

7. The process of claim 6, wherein the solvent is selected from vegetable oils, plant oils, animal oils, essential oils, mineral oils, $C_7$ to $C_{40}$ isoparaffins, alkyl carboxylic esters, jojoba oil, and shark liver oil.

8. The process of claim 1, wherein the composition comprises at least 5 wt. % ethylene carbonate.

9. The process of claim 1, wherein heating device comprises a flat iron.

10. The process of claim 1, further comprising drying the hair fibers to remove at least a portion of the solvent prior to contacting the coated hair fibers with a heating device.

11. The process of claim 1, wherein the coating of the hair fibers with the composition comprises contacting the hair fibers with said composition for at least 30 minutes.

* * * * *